United States Patent
Zhang et al.

(10) Patent No.: US 10,294,199 B2
(45) Date of Patent: May 21, 2019

(54) PROPYL CATIONIC PEPTIDE LIPIDS, SYNTHESIS METHOD THEREOF, AND APPLICATION THEREOF

(71) Applicant: DALIAN NATIONALITIES UNIVERSITY, Dalian, Liaoning (CN)

(72) Inventors: Shubiao Zhang, Liaoning (CN); Yinan Zhao, Liaoning (CN); Shaohui Cui, Liaoning (CN); Defu Zhi, Liaoning (CN); Hua Hai, Liaoning (CN)

(73) Assignee: DALIAN NATIONALITIES UNIVERSITY, Dalian, Liaoning (CN)

( * ) Notice: Subject to any disclaimer, the term of this patent is extended or adjusted under 35 U.S.C. 154(b) by 12 days.

(21) Appl. No.: 15/542,268

(22) PCT Filed: Jun. 25, 2015

(86) PCT No.: PCT/CN2015/082261
§ 371 (c)(1),
(2) Date: Jul. 7, 2017

(87) PCT Pub. No.: WO2016/192150
PCT Pub. Date: Dec. 8, 2016

(65) Prior Publication Data
US 2017/0355667 A1 Dec. 14, 2017

(30) Foreign Application Priority Data

Jun. 4, 2015 (CN) .......................... 2015 1 0304228

(51) Int. Cl.
| | |
|---|---|
| *C07K 5/00* | (2006.01) |
| *C09K 17/02* | (2006.01) |
| *C12N 15/87* | (2006.01) |
| *C12N 15/88* | (2006.01) |
| *C07C 269/06* | (2006.01) |
| *C07C 271/20* | (2006.01) |

(52) U.S. Cl.
CPC .......... *C07C 269/06* (2013.01); *C07C 271/20* (2013.01); *C07K 5/00* (2013.01); *C09K 17/02* (2013.01); *C12N 15/87* (2013.01); *C12N 15/88* (2013.01)

(58) Field of Classification Search
CPC .............. A61K 48/0041; C07C 269/06; C07C 271/20; C07K 5/00; C09K 17/02; C12N 15/87; C12N 15/88
See application file for complete search history.

(56) References Cited

U.S. PATENT DOCUMENTS

2002/0007073 A1 1/2002 Schneider et al.

FOREIGN PATENT DOCUMENTS

| CN | 103553970 | 2/2014 |
|---|---|---|
| WO | WO9640627 | 12/1996 |

OTHER PUBLICATIONS

Hwang et al., "Relative Reactivities of Amino Acids in Pyrazine Formation," J. Agric. Food Chem. 1995, 43, 179-184 (Year: 1995).*
Chen, Meling, "Synthesis and biological properties of peptided lipids," Thesis of Liaoning Normal University, China, Apr. 2013. (Year: 2013).*
Partial English translation of Chen, Meling, "Synthesis and biological properties of peptided lipids," Thesis of Liaoning Normal University, China, Apr. 2013, pp. 1-29 (Year: 2013).*
Chen, Meiling; "Synthesis and biological properties of peptided lipids", Graduate Student Thesis of Liaoning Normal University, Liaoning, China; Apr. 2013; 67 pages; Medicine & Public Health, China Master's Theses Full-Text Database, No. 5, May 15, 2014 (May 15, 2014), E060-168.
International search report dated Mar. 2, 2016 from corresponding application No. PCT/CN2015/082261.

* cited by examiner

*Primary Examiner* — Pancham Bakshi
*Assistant Examiner* — Mark R Luderer
(74) *Attorney, Agent, or Firm* — Hauptman Ham, LLP

(57) ABSTRACT

A class of propyl cationic peptide lipids is propyl cationic peptide lipid compounds having a general formula structure as follows. After the propyl cationic peptide lipids are dispersed in water, a cationic liposome with a particle size of approximately 100 nm is obtained. The cationic liposome can carry plasmid DNA (pDNA) or small interfering RNA (siRNA) into cells to realize the function of gene delivery, and is almost non-toxic to the cells.

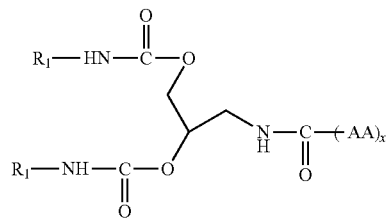

11 Claims, 12 Drawing Sheets

PROPYL CATIONIC PEPTIDE LIPIDS, SYNTHESIS METHOD THEREOF, AND APPLICATION THEREOF

RELATED APPLICATIONS

The present application is a National Phase of International Application Number PCT/CN2015/082261, filed Jun. 25, 2015, and claims the priority of China Application No. 201510304228.4, filed Jun. 4, 2015.

TECHNICAL FIELD

The invention pertains to the field of biotechnology, particularly relates to a non-viral gene vector and a preparation method thereof.

BACKGROUND ART

Gene therapy is to correct or compensate for defects of genes, shut down or inhibit the expression of abnormal genes by introducing an exogenous gene DNA or RNA fragment to target cells or tissues, so as to achieve the purpose of treating diseases. As a new therapeutic means, gene therapy can treat various diseases, including cancer, genetic disorders, infectious diseases, cardiovascular diseases and autoimmune diseases. Wherein, cancer gene therapy is the main application field of gene therapy. During the development of gene therapy for decades, there are nearly 2000 cases of clinical trials of gene-transfected gene therapy launched in all over the world. In 1990, Culver et al. from National Institutes of Health first applied gene therapy to clinical trials, and they by a gene therapy method treated adenosine deaminase (ADA) deficiency and succeeded. In 2000, French successfully used the technology of gene therapy to cure Combined Immunodeficiency Syndrome (X-SCID), thereby confirming the effectiveness of gene therapy strategy. However, if the gene therapy would like to get further development, there are the following three problems we must overcome: firstly, there must be a target gene for treatment and a cell accepting the target gene; secondly, to realize the regulatability of gene expression; thirdly, obtain targeted gene vector system with high efficiency and low toxicity. Among them, the targeted gene vector system with high efficiency is one of the bottlenecks restricting the development of gene therapy.

Cationic liposomes have cell-like structures and characteristics of biofilm, they can be degraded in vivo and can protect biological activity of gene fragments carried by them, so they are non-viral gene transfection vectors with a clinical application potentiality. Such structures of liposomes make it possible to enclose drug powder or compress genes to form complexes and deliver them to diseased tissues or cells, after entering into the human body, they are mainly phagocytosed by a reticuloendothelial system to activate the body's own immune function and to change in-vivo distribution of the encapsulated drug, in order that the drug is mainly accumulated in the liver, spleen, lung and bone marrow and other tissues and organs, thereby improving the therapeutic index of the drug, reducing the therapeutic dose of the drug and reducing the toxicity of the drug. Since 1987 Felgner et al. first using N-[1-(2,3-dioleyloxy)propyl]-N,N,N-trimethyl ammonium chloride (DOTMA) successfully transfected cells such as COS-7 etc., liposome has been developed to be the most widely used gene delivery methods in addition to retroviral vectors, and more particularly in the treatment of diseases such as tumors and cystic fibrosis, etc. However, because it still has some limitations, for example, the high cell toxicity, organ targeting is not obvious, the gene transfer mechanism is unclear, and these limit its wider application. Therefore, people have been working on various constructions and chemical modifications of cationic liposomes, seeking to find a gene therapy vector with high efficiency and low toxicity.

For nearly 30 years development of liposomes, from widely used cationic lipid with quaternary ammonium salt head, guanidino head to cationic lipid with polyamine head, there has been formed relatively complete liposome vector systems, but these vector systems still have many problems, for example, the transportation efficiency of mediated gene needs to be improved; lack of directional recognition for target tissues; after cationic liposomes/DNA complexes entering into a cell, nucleic acid is bound inside the endosome and can hardly be released, which is unfavorable for the expression in cytoplasm or nucleus, thereby making it impossible to achieve therapeutic purposes. A Chinese invention patent CN103553970A, Feb. 5, 2014, discloses preparation of urethane-type cationic lipid and application of the same in drugs or gene transportation, although this vector has an efficient gene transportation capability, it has certain cytotoxicity due to its structure of a quaternary ammonium salt head, so it is limited in the aspect of gene transportation in vivo.

SUMMARY OF INVENTION

An object of the invention is to provide a propyl cationic peptide lipid which has little cytotoxicity and the high transfecting efficiency for in vitro gene, and to provide a synthesis method and application of the same.

The technical solution of the invention is as follows.

I. Propyl Cationic Peptide Lipid and Preparation Method Thereof

1. A propyl cationic peptide lipid of which the chemical structure is represented by a general formula I:

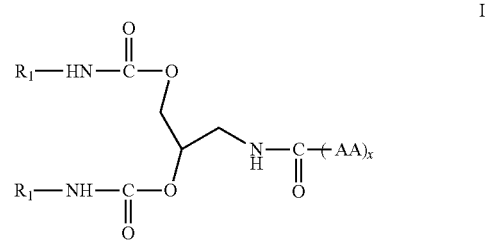

wherein,
$R_1$ is selected from $C_{1-20}$ alkyl, most preferably $C_{12}$, $C_{14}$, $C_{16}$ or $C_{18}$;
x is selected from 1 to 6, most preferably 2 to 4;
AA is selected from Lys, Orn, Arg, His, Asp, Ala or Gly.

2. A method for synthesizing a propyl cationic peptide lipid, comprising: preparing a peptide head intermediate using amino acid with amino protecting; acylating amino protected 3-amino-1,2-propanediol with an acylating agent and then reacting the resultant with alkyl amine, to prepare a double long carbon chain intermediate; linking the prepared peptide head intermediate with the prepared double long carbon chain intermediate via acylation; releasing the protective group and then reacting the resultant with the amino protected amino acid, after de-protection, to obtain said propyl cationic peptide lipid compound.

Specific steps are as follows.

(1) Preparing the amino acid head intermediate by protecting amino group of amino acid with a protective reagent by means of orthogonal protection method; said amino acid is lysine, histidine, ornithine or arginine; said protective reagent is $Boc_2O$, Fmoc-OSu or CbzCl, etc.; a molar ratio of said protective reagent and said amino acid is 1:1 to 8:1; the reaction solvent is acetonitrile, water, tetrahydrofuran, toluene, acetone or a mixture of the above solvents, etc., the reaction time is 1 to 20 hours, and the reaction temperature is 0 to 100° C. After the reaction, the solvent is removed by rotary evaporation, followed by purification by means of recrystallization with a recrystallization solvent being an ethyl acetate/petroleum ether mixed solvent (v/v=3:1).

(2) Protecting the amino group of 3-amino-1,2-propanediol with Fmoc-OSu protective reagent, after acylation with an acylating agent, reacting the resultant with alkyl amine, to prepare a disubstituted propyl long carbon chain intermediate; said acylating agent is carbonyl diimidazole; a molar ratio of the acylating agent and 3-amino-1,2-propanediol is 1:1 to 3:1; after acylation, the molar ratio of 3-amino-1,2-propanediol to the alkyl amine is from 1:1 to 8:1; the reaction solvent is 30 ml to 300 ml of toluene, dichloromethane, DMF or chloroform, the reaction time is 12 to 48 hours, and the reaction temperature is 25~100° C. After the reaction, the solvent is removed by rotary evaporation at 70° C., and recrystallization is carried out with DMF, ethyl acetate, ethanol, water or ethanol/water mixed solvent.

(3) Linking the peptide head intermediate prepared in step (1) with the double long carbon chain intermediate prepared in step (2) via acylation: a. firstly, activating the peptide head intermediate with an activating agent which is 2-(7-azobenzotriazole)-N,N,N',N'-tetramethyluronium hexafluorophosphate (HATU), N,N'-dicyclohexyl carbonimide (DCC) or 1-hydroxybenzotriazole (HOBt), a molar ratio of the peptide head intermediate to the activating agent being 1:1 to 1:8, the reaction temperature being 0 to 60° C., and the reaction time being 0.5 to 24 hours. b. Adding a solution of the double long carbon chain intermediate in dichloromethane, DMF or chloroform to the reaction solution in step a; after acylation, an amide bond is generated between the amino group of the intermediate and the carboxyl group of the peptide head intermediate; the peptide head intermediate reacts with the long carbon chain intermediate at a molar ratio from 1:1 to 8:1; the reaction solvent is toluene, DMF, chloroform, acetone or methylene chloride, the reaction time is 12 to 96 hours, and the reaction temperature is 20 to 100° C.

(4) Removing the protective group with an amino de-protection agent which is 10% $NaHCO_3$ (w/v) or trifluoroacetic acid; a molar ratio of the de-protection agent and a lipid compound is 1:1 to 1:2, the de-protection time is 1 to 8 hours, and the de-protection temperature is 0 to 4° C.; the product is purified by recrystallization to obtain a crude product; wherein the recrystallization solvent is ethyl acetate, acetonitrile, ethanol, water or anhydrous ether.

(5) After the recrystallization, purification is carried out by column chromatography; the crude product is dissolved in chloroform and purified with a silica gel column, followed by elution with a mixed solvent of methanol/chloroform (at a volume ratio of 3:1). The solvent is removed by rotary evaporation, followed by lyophilization, to obtain a cationic peptide lipid compound containing one amino acid head.

(6) Synthesizing another propyl cationic peptide lipid using the cationic peptide lipid compound containing one amino acid head as raw material: subjecting the peptide head intermediate prepared in step (1) and the cationic peptide lipid compound containing one amino acid head prepared in step (5) to amino activation and acylation, to obtain a cationic peptide lipid compound of which the head is 1 to 4 amino acid(s). A molar ratio of the two is 1:8 to 8:1, and the specific reaction conditions and purification method are the same as steps (3), (4) and (5).

II. Cationic Peptide Liposome and Preparation Method Thereof

1. A cationic peptide liposome prepared from said propyl cationic peptide lipid, which is a homogeneous and stable liposome which is positively charged on the surface thereof and has a particle size of about 100 nm formed by dispersing the propyl cationic peptide lipid in an aqueous phase.

2. A preparation method of a propyl cationic peptide liposome, comprising steps as follows: mixing said propyl cationic peptide lipid compound and an additive in an organic solvent such as chloroform, methanol, so that the concentration of the propyl cationic peptide lipid compound is 1 to 8 mg/ml. Blow-drying the solution under nitrogen to form an uniform thin film, which is dried in vacuum for 2 to 24 hours (at a vacuum degree of 0.09 MPa, room temperature); adding ultrapure water, ethanol or phosphate buffer, performing hydration at 10 to 80° C. for 1 to 10 hours, ultrasonic vibrating at the ultrasonic frequency of 100 Hz to be clear and transparent, and the concentration of said cationic peptide liposome is 0.5 to 3 mg/ml. Said additive is lecithin, sucrose esters, dioleoyl phosphatidylethanolamine (DOPE), dioleoyl phosphatidylcholine (DOPC) or cholesterol.

III. Propyl Cationic Peptide Liposome/Gene Complex and Preparation Method Thereof 1. Propyl cationic peptide liposome/gene complexes are homogeneous and stable nanoparticles dispersed in an aqueous phase, which are formed by electrostatic interaction between said propyl cationic peptide liposome and pDNA or siRNA.

2. A method for preparing a propyl cationic peptide liposome/gene complex, comprising steps as follows:

(1) taking said propyl cationic peptide liposome and dispersing it in a cell culture medium (DMEM or RPMI1640), mixing homogeneous to make the concentration being 0.02 μg/μl to 0.16 μg/μl;

(2) diluting 0.5 to 1.0 μg pDNA or siRNA in the cell culture medium DMEM or RPMI1640, mixing homogeneous to make the plasmid concentration being 0.02 μg/μl;

(3) mixing the two dilutions (1) and (2) according to a mass ratio between the liposome and gene of 1:1 to 8:1, placing at a room temperature for 10 to 40 min, to obtain a propyl cationic peptide liposome/gene complex.

IV. Use of Said Propyl Cationic Peptide Liposome/Gene Complex for Cell Transfection, Mainly Including:

(1) Said propyl cationic peptide liposome/gene complex can enter into cancer cells and accomplish transfection of a target gene in cells.

(2) Said cells are human laryngeal epithelial cell (Hep-2) and non-small lung adenocarcinoma cell (A549). The peptide liposome/gene complexes obtained at different nitrogen-phosphorus ratios will have different transfection efficiency in different cells.

(3) The propyl peptide liposome/gene complex provided by the invention is applicable to pDNA comprising reporter genes encoding such as luciferase, green fluorescent protein, also applicable to other siRNAs required by various experiments. The vector can efficiently carry plasmid DNA and siRNA to transfect cells.

The action mechanism of the invention is substantially as follows: a propyl peptide lipid provided by the invention has both hydrophobic and hydrophilic properties; the hydrophobic moiety is derived from propyl double long carbon chain, and the hydrophilic moiety is derived from a lipid head made of amino acid or peptide having good biocompatibility. Because amino acid or peptide has a multiple amino structure, it can combine with negatively charged nucleic acids, so nucleic acids can be effectively compressed, at the same time it has good affinity for cells, thereby improving the transfection efficiency of the vector. In addition, amino acids and peptides are essential substances for the organism, can reduce the toxicity caused by the polar head of the cationic quaternary ammonium salt lipid.

The invention has the following advantages compared with the prior art.

1. The synthesis method of the propyl cationic peptide lipid of the invention is simple, the reaction reagents used and the product obtained are non-toxic and non-polluting, and the cost of the raw materials is low, so it can be easily popularized; during the reaction, the reaction conditions are mild, by-products are less and purification is easy; it can be widely used in scientific research and production.

2. The propyl cationic peptide liposome provided by the invention is rich in cations, has a capability of compressing plasmid DNA and siRNA and can form a nano-scale cationic liposome/gene complex. Said propyl cationic peptide liposome/gene complex is acid sensitive, which may facilitate the release of genes and improve the transfection efficiency. The cationic head of the propyl cationic peptide liposome is a peptide composed of lysine, histidine, arginine or ornithine, which is one of essential amino acids for human body and has good biodegradability, so the toxicity caused by the cationic head is reduced.

3. The propyl cationic peptide liposome provided by the invention has good stability, a particle size of about 100 nm, and a Zeta potential between 40~70 mV; it can compress much more negatively charged genetic materials, improve in-vitro or in-vivo transfection efficiency; it has good cell compatibility and less toxicity, and can be used as a novel efficient and low toxic non-viral gene vector and transfection reagent.

As compared with the urethane-type cationic liposome (DDCTMA) in the Chinese invention patent CN103553970A, the propyl cationic peptide liposome provided by the invention has high transfection efficiency and low toxicity, and it has the transfection efficiency equivalent to that of a commercial reagent Lipofectamine 2000 and the toxicity equivalent to that of DOTAP (Lipofectamine 2000 and DOTAP are standard control reagents, Lipofectamine 2000 has relatively higher transfection efficiency, and DOTAP ha1s relatively less toxicity).

4. The propyl cationic peptide liposome/gene complex provided by the invention is expected to become a novel gene vector used for clinical gene therapy.

DETAILED DESCRIPTION OF EMBODIMENTS

Figure 1:
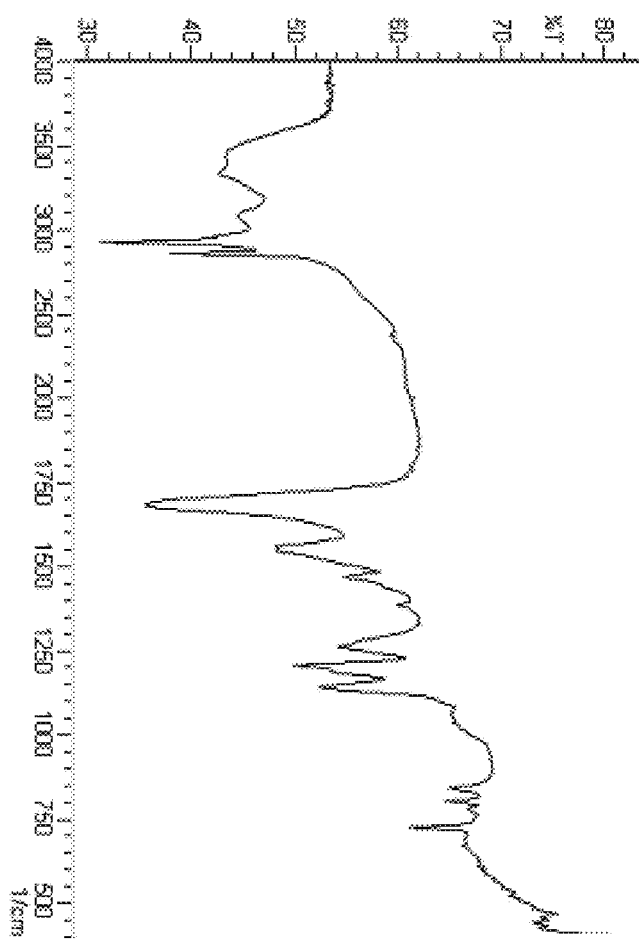
FIG. 1 is an infrared spectra of a propyl peptide lipid compound $R_{12}O$.

To be helpful for further understanding the invention, preferable embodiments of the invention are described in combination with the following examples, but the following description is not a limitation to the claims of the invention but merely is further interpretation of features and advantages of the invention.

In this specification, the description is made by taking the following four kinds of propyl cationic peptide lipid compounds as examples: N-(1,2-bis-dodecyl amino formyloxopropyl) ornithine amide represented by $R_{12}O$, containing an Orn cationic head, a urethane linkage and a 14 carbon propyl double hydrophobic tail chain; N-(1,2-bis-tetradecylamino formyloxypropyl) alanine ornithine amide ($R_{14}AO$) containing an Ala-Orn dipeptide cationic head, a urethane linkage and a 14 carbon propyl double hydrophobic tail chain; N-(1,2-bis-hexadecylamino formyloxypropyl) ornithine dimeric lysine amide ($R_{16}OKK$) containing an Orn-Lys-Lys tripeptide cationic head, a urethane linkage and a 16 carbon propyl double hydrophobic tail chain; N-(1,2-bis-octadecylamino formyloxypropyl) alanine-ornithine-dimeric lysine amide ($R_{18}AOKK$) containing an Ala-Orn-Lys-Lys tetrapeptide cationic head, a urethane linkage and a 18 carbon propyl double hydrophobic tail chain.

Example 1

A synthesis method of the cationic peptide lipid compound $R_{12}O$ is as follows.

(1) 2 mmol L-Orn was weighted and dissolved in 15 ml of acetonitrile; 16 mmol $Boc_2O$ was dissolved in acetonitrile and added dropwise to an acetonitrile solution of ornithine, to react and generate a complex; 10 ml 20% sodium bicarbonate aqueous solution was added, and 2 g of anhydrous sodium carbonate and an appropriate amount of 8-hydroxyquinoline were added in batches; the mixture was stirred and reacted at room temperature for 4 hours to remove copper ions in the complex; then 2 mmol Fmoc-OSu was added to the aforesaid solution, followed by stirring at room temperature for 2 hours; the resultant was recrystallized with an ethyl acetate/petroleum ether mixed solvent, to obtain a peptide head intermediate Fmoc-L-Orn (Boc)-OH.

(2) 10 mmol 3-amino-1,2-propanediol was dissolved in 50 ml water, 10 mmol sodium bicarbonate was added, and then 10 mmol Fmoc-OSul was dissolved in 100 ml of acetone, slowly added dropwise and stirred overnight. Acetone was distilled off by rotary evaporation. 8.0 mmol of the above product was dissolved in a dichloromethane/toluene mixed solvent; 8.0 mmol CDI was dissolved in toluene, and the two were slowly added dropwise under protection by nitrogen to react at 25° C. for 12 hours. 1 mmol dodecylamine was dissolved in 5 ml toluene solution, and the mixture was slowly added dropwise to the aforesaid reaction solution, and reaction was further carried out at 25° C. for 24 hours. 3.0 mmol sodium hydroxide was added to the reaction solution to react for 1 hour. After completion of the reaction, the solvent was removed by rotary evaporation at 70° C., followed by recrystallization with acetonitrile/water (v/v=5:1), to obtain pale yellow solid, which was dried under vacuum. The resultant was recrystallized with DMF once again, to obtain a double long carbon chain intermediate $R_{12}$.

(3) The prepared peptide head intermediate Fmoc-L-Orn (Boc)-OH and an activating agent HATU were dissolved at a molar ratio of 1:8 in a toluene solution, and the activation was carried out at 0° C. for 24 hours, and then a toluene solution of the double long carbon chain intermediate $R_{12}$ was added so that the peptide head intermediate reacted with the double long carbon chain intermediate according to a molar ratio of 8:1, followed by amidation reaction at 20° C. for 96 hours; after the reaction was completed, the solvent was removed by rotary evaporation at 70° C. The resultant was dissolved with a solvent of dichloromethane/trifluoroacetic acid=2/1 (v/v), and placed at 4° C. for 8 h to release the protective group Boc; then the product was dissolved by 20 ml 10% $NaHCO_3$ solvent, reacted for 1 hour, to remove Fmoc group.

Figure 2:
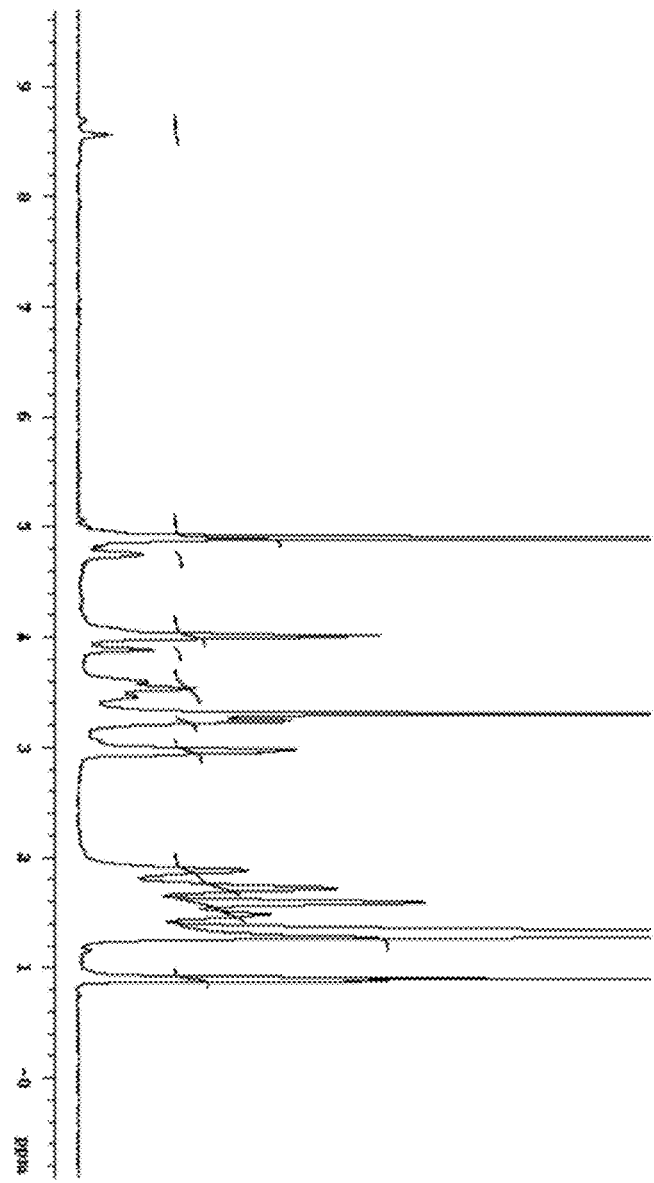
FIG. 2 is a nuclear magnetic resonance hydrogen spectrum of a propyl peptide lipid compound $R_{12}O$.

(4) After being recrystallized with ethyl acetate and acetonitrile for four times, the product was dissolved in chloroform, and the crude product was purified by a silica gel column and then was eluted with a methanol/chloroform (volume ratio 3:1) mixed reagent. The solvent was removed by rotary evaporation, and the resultant was lyophilized, to obtain a propyl cationic peptide lipid $R_{12}O$ containing one ornithine head and a 12C double long carbon chain, of which the structural characterization is shown by FIG. 1 and FIG. 2.

Its structure is characterized as below: $^1H$ NMR (400 MHz, $CD_3OD$) δ:0.86 (6H, $CH_3$), 1.25 (36H, $(CH_2)_9$), 2.95 (2H, $CH_2NH_2$), 3.08 (2H, $CH_2NH$), 3.30 (2H, $OCHCH_2$), 3.93 (2H, $CHNH_2$), 4.01 (2H, $OCH_2CH$), 5.02 (1H, $OCHCH_2$). $^{13}C$ NMR (400 MHz, $CD_3OD$) δ: 12.98 ($CH_3$), 23.09 ($CH_3CH_2$), 30.02 (($CH_2)_8$), 37.98 ($CH_2NH$), 40.13 ($CH_2NHCH$), 40.75 ($CH_2NH_2$), 52.76 ($CHNH$, $CHNH_2$), 63.91 ($OCH_2CH$), 71.45 ($OCH_2CHO$), 158.80 (NHCOO), 169.15 (NHCOCH). IRv/$cm^{-1}$: 3289 ($v_{NH}$), 2930 ($v_{CH}$), 1679 ($v_{C=O}$), 1540 ($δ_{NH}$), 1190 ($v_{CN}$).

Example 2

A synthesis method of the cationic peptide lipid compound $R_{14}AO$ is as follows.

(1) 10 mmol L-Ala was weighted and dissolved in 100 ml of acetonitrile; 12 mmol $Boc_2O$ was dissolved in acetonitrile and added dropwise to an acetonitrile solution of Ala; the mixture was stirred and reacted at room temperature for 2 hours, and then the solvent was removed by rotary evaporation at 70° C., followed by recrystallization with an ethyl acetate/petroleum ether mixed solvent, to obtain a peptide head intermediate L-Ala (Boc)-OH.

(2) 10 mmol 3-amino-1,2-propanediol was dissolved in 50 ml water, 10 mmol sodium bicarbonate was added, and then 20 mmol Fmoc-OSul was dissolved in 100 ml acetone, slowly added dropwise and stirred overnight. Acetone was distilled off by rotary evaporation. 5.0 mmol of the above product was dissolved in a dichloromethane/toluene mixed solvent; 5.0 mmol CDI toluene solution was added under protection by nitrogen to react at 80° C. for 2 hours. 12 mmol toluene solution of tetradecylamine was slowly added dropwise to the aforesaid reaction solution, and reaction was further carried out at 80° C. for 2 hours. 3.0 mmol sodium hydroxide was added to the reaction solution to react for 1 h. After completion of the reaction, the solvent was removed by rotary evaporation at 70° C., followed by recrystallization with acetonitrile/water (v/v=5:1), to obtain pale yellow solid. The resultant was recrystallized with DMF once again, to obtain a double long carbon chain intermediate $R_{14}$.

(3) The prepared peptide head intermediate L-Ala (Boc)-OH and an activating agent HATU were dissolved at a molar ratio of 1:1 in a toluene solution, and the activation was carried out at 60° C. for 0.5 hour, and then a toluene solution of the double long carbon chain intermediate $R_{14}$ was added (the peptide head intermediate and the long carbon chain intermediate reacted according to a molar ratio of 1:1); followed by amidation reaction at 40° C. for 48 hours; after the reaction was completed, the solvent was removed by rotary evaporation at 70° C. The resultant was dissolved with a solvent of dichloromethane/trifluoroacetic acid=3/1 (v/v), and placed at 4° C. for 2 hours to release the protective group Boc; then the product was dissolved by a dioxane solvent, and 2 ml 10% $NaHCO_3$ was added to react for 2 hours, to remove Fmoc group; then the solvent was removed by rotary evaporation at 70° C.

(4) The product was recrystallized with acetonitrile twice and then recrystallized with ethyl acetate twice. After that, the product was dissolved in chloroform, and the crude product was purified by a silica gel column and then was eluted with a methanol/chloroform (volume ratio 3:1) mixed reagent. The solvent was removed by rotary evaporation at 70° C., and the resultant was lyophilized, to obtain a propyl cationic peptide lipid compound containing one alanine head.

(5) 10 mmol L-Orn was weighted and dissolved in 30 ml acetonitrile, and 20 mmol $Boc_2O$ was dissolved in acetonitrile, and the mixture was added dropwise to the acetonitrile solution of ornithine, and a complex was generated after reaction. 15 ml 10% sodium bicarbonate aqueous solution was added, and 3 g of anhydrous sodium carbonate and an appropriate amount of 8-hydroxyquinoline were added in batches; the mixture was stirred and reacted at 30° C. for 2 hours to remove copper ions in the complex; then 12 mmol Fmoc-OSu was added to the aforesaid solution, followed by stirring at 30° C. for 2 hours; the solvent was removed by rotary evaporation after the reaction completed, and the resultant was recrystallized twice with an ethyl acetate/petroleum ether system, to obtain a peptide head intermediate Fmoc-L-Orn (Boc)-OH.

(6) The cationic peptide lipid compound containing one alanine head prepared in step (4) reacted with the amino protected ornithine peptide heat intermediate Fmoc-L-Orn (Boc)-OH prepared in step (5) at a molar ratio of 8:1, followed by amino acid activation and amidation, to obtain a propyl cationic peptide lipid $R_{14}AO$ containing an Ala-Orn dipeptide cationic head and a 14C double long carbon chain.

Figure 3:
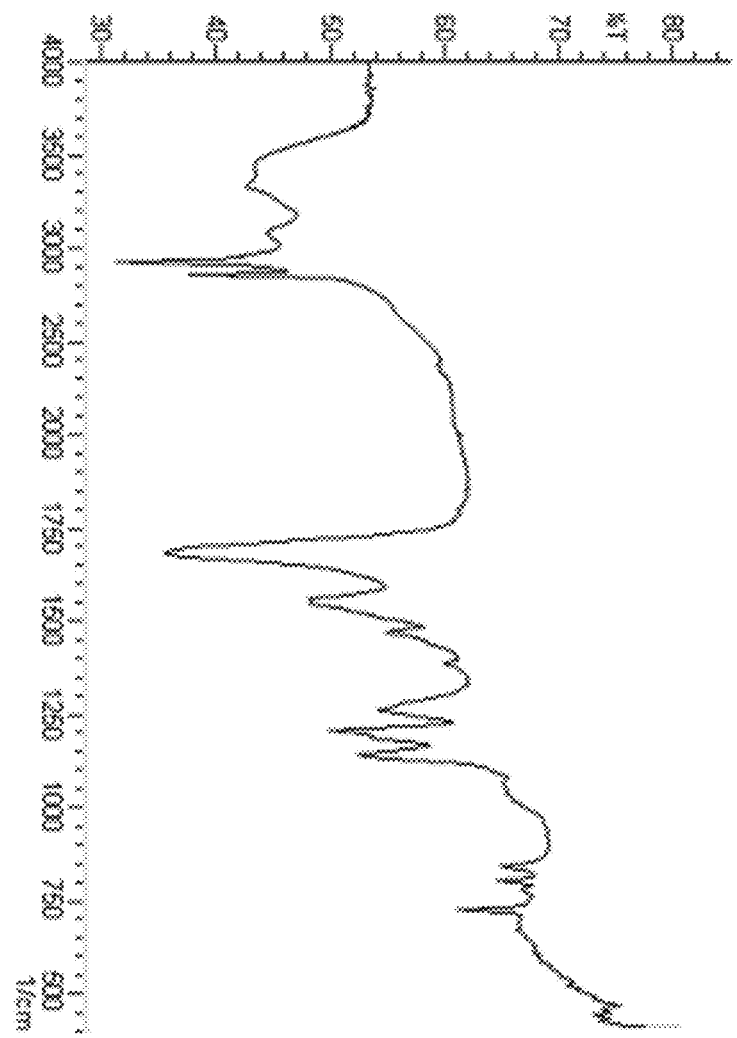
FIG. 3 is an infrared spectra of a propyl peptide lipid compound $R_{14}AO$.
Figure 4:
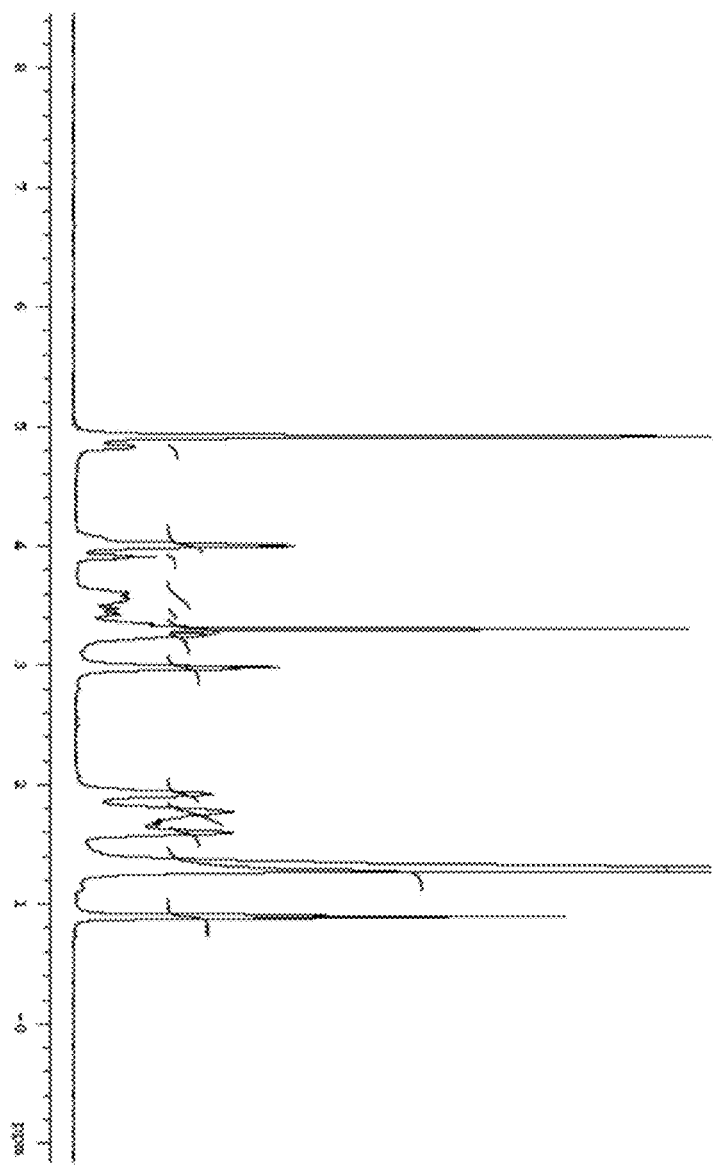
FIG. 4 is a nuclear magnetic resonance hydrogen spectrum of a propyl peptide lipid compound $R_{14}AO$.

Specific reaction conditions and purification method are the same with steps (3) and (4), and the structural characterization is shown by FIG. 3 and FIG. 4.

Its structure is characterized as below: $^1$H NMR (400 MHz, CD$_3$OD) δ: 0.88 (6H, CH$_3$), 1.26 (44H, (CH$_2$)$_{11}$), 2.89 (2H, CH$_2$NH$_2$), 3.06 (2H, CH$_2$NH), 3.32 (2H, OCHCH$_2$), 3.93 (2H, CHNH$_2$), 4.04 (2H, OCH$_2$CH), 4.97 (1H, OCHCH$_2$). $^{13}$C NMR (400 MHz, CD$_3$OD) δ: 12.91 (CH$_3$), 22.98 (CH$_3$CH$_2$), 30.04 ((CH$_2$)$_{10}$), 38.18 (CH$_2$NH), 39.56 (CH$_2$NHCH), 40.71 (CH$_2$NH$_2$), 52.79 (CHNH, CHNH$_2$), 63.96 (OCH$_2$CH), 71.24 (OCH$_2$CH), 158.12 (NHCOO), 168.55 (NHCOCH). IRv/cm$^{-1}$: 3320 ($v_{NH}$), 2900 ($v_{C=O}$), 1675 ($v_{C=O}$), 1540 ($δ_{NH}$), 130 ($v_{CN}$).

Example 3

A synthesis method of the cationic peptide lipid compound R$_{16}$OKK is as follows.

(1) 10 mmol L-Orn was weighted and dissolved in 15 ml of acetonitrile; 80 mmol Boc$_2$O was dissolved in acetonitrile, and the mixture was added dropwise to an acetonitrile solution of ornithine, and a complex was generated after reaction; 20 ml 20% sodium bicarbonate aqueous solution was added, and 2 g of anhydrous sodium carbonate and an appropriate amount of 8-hydroxyquinoline were added in batches; the mixture was stirred and reacted at room temperature for 4 hours to remove copper ions in the complex; then 10 mmol Fmoc-OSu was added to the aforesaid solution, followed by stirring at room temperature for 2 hours; the resultant was recrystallized with an ethyl acetate/petroleum ether mixed solvent, to obtain a peptide head intermediate Fmoc-L-Orn (Boc)-OH.

(2) 5 mmol 3-amino-1,2-propanediol was dissolved in 50 ml acetone, 5 mmol sodium bicarbonate was added, and then 7 mmol Fmoc-OSul was dissolved in 50 ml of acetone, slowly added dropwise and stirred overnight. Acetone was distilled off by rotary evaporation. 2.0 mmol of the above product was dissolved in a dichloromethane solvent; 2.0 mmol CDI was dissolved in toluene, and the two were slowly added dropwise under protection by nitrogen to react at 40° C. for 24 hours. 2 mmol hexadecylamine was dissolved in 10 ml toluene solution, and the mixture was slowly added dropwise to the aforesaid reaction solution, and reaction was further carried out at 40° C. for 48 hours. 5.0 mmol sodium hydroxide was added to the reaction solution to react for 2 hours. After completion of the reaction, the solvent was removed by rotary evaporation at 70° C., followed by recrystallization with acetonitrile/water (v/v=5: 1), to obtain pale yellow solid, which was dried under vacuum. The resultant was recrystallized with DMF once again, to obtain a double long carbon chain intermediate R$_{16}$.

(3) The prepared peptide head intermediate Fmoc-L-Orn (Boc)-OH and an activating agent HATU were dissolved at a molar ratio of 1:2 in a toluene solution, and the activation was carried out at room temperature for 2 hours, and then a toluene solution of the double long carbon chain intermediate R$_{16}$ was added so that the peptide head intermediate reacted with the double long carbon chain intermediate according to a molar ratio of 1:2, followed by amidation reaction at 40° C. for 48 hours; after the reaction was completed, the solvent was removed by rotary evaporation at 70° C. The resultant was dissolved with a solvent of dichloromethane/trifluoroacetic acid=2/1 (v/v), and placed at 4° C. for 1 hour to release the protective group Boc; then the product was dissolved by a dioxane solvent; then 30 ml 10% NaHCO$_3$ solvent was added and reacted for 2 hours, to remove Fmoc group.

(4) After the product was recrystallized with acetonitrile and then recrystallized with petroleum ether four times, the product was dissolved in chloroform, and the crude product was purified by a silica gel column and then was eluted with a methanol/chloroform (volume ratio 3:1) mixed reagent. The solvent was removed by rotary evaporation at 70° C., and the resultant was lyophilized, to obtain a propyl cationic peptide lipid compound containing one ornithine head.

(5) 2 mmol L-Lys was weighted and dissolved in 15 ml of acetonitrile; 2 mmol Boc$_2$O was dissolved in acetonitrile, and then the mixture was added dropwise to an acetonitrile solution of lysine; 1 mmol copper sulfate pentahydrate was added, and (LysBoc)$_2$Cu complex was generated after the reaction; 10 ml 20% sodium bicarbonate aqueous solution was added, and 2 g of anhydrous sodium carbonate and an appropriate amount of 8-hydroxyquinoline were added in batches; the mixture was stirred and reacted at room temperature for 4 hours to remove copper ions in the complex; then 2 mmol Fmoc-OSu was added to the aforesaid solution, followed by stirring at room temperature for 2 hours; the resultant was recrystallized with an ethyl acetate/petroleum ether system, to obtain a peptide head intermediate Fmoc-L-Lys (Boc)-OH.

Figure 5:
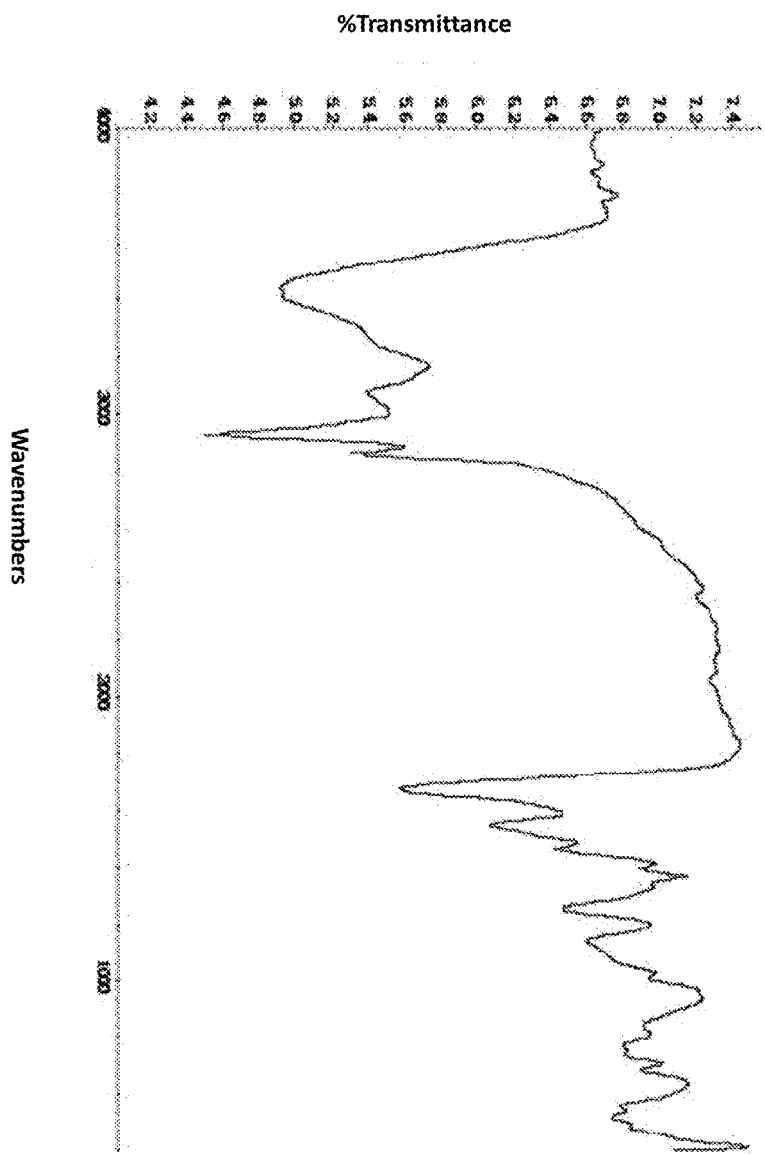
FIG. 5 is an infrared spectra of a propyl peptide lipid compound $R_{16}OKK$.
Figure 6:
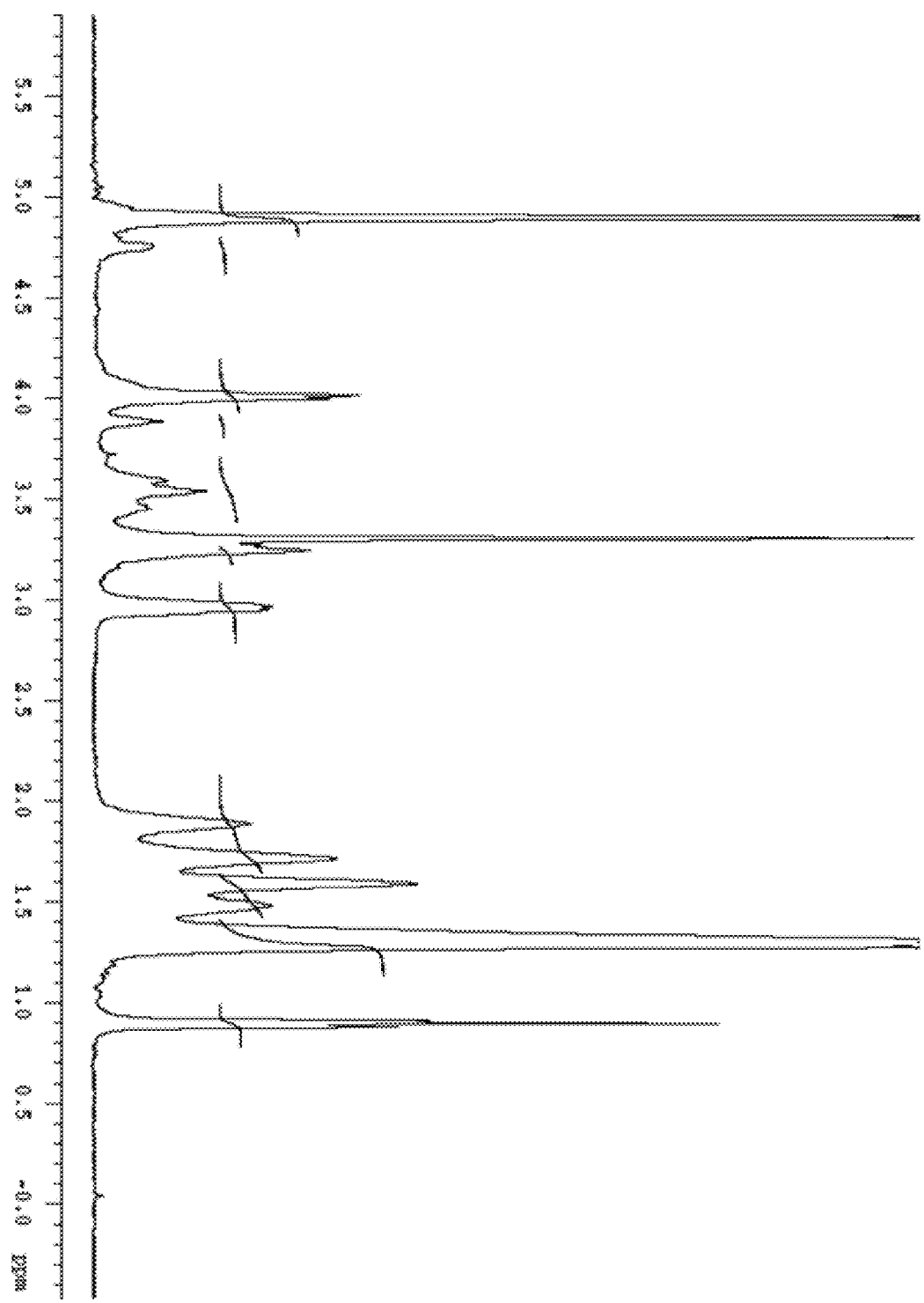
FIG. 6 is a nuclear magnetic resonance hydrogen spectrum of a propyl peptide lipid compound $R_{16}OKK$.

(6) The cationic peptide lipid compound containing one ornithine head was taken as a raw material to react with the amino protected lysine heat intermediate prepared in step (5) at a molar ratio of 1:2, followed by amino acid activation and amidation; wherein the specific reaction conditions and purification method are the same with steps (3) and (4). A propyl cationic peptide lipid R$_{16}$OKK containing a cationic head with a structure of one ornithine and two lysines, and a 16C double long carbon chain, is obtained, of which the structural characterization is shown by FIG. 5 and FIG. 6.

Its structure is characterized as below: $^1$H NMR (400 MHz, CD$_3$OD) δ: 0.89 (6H, CH$_3$), 1.29 (52H, (CH$_2$)$_{13}$), 2.90 (4H, CH$_2$NH$_2$), 3.18 (6H, CH$_2$NH), 3.33 (2H, OCHCH$_2$), 3.93 (2H, CHNH$_2$), 4.15 (2H, OCH$_2$CH), 4.88 (1H, OCHCH$_2$). $^{13}$C NMR (400 MHz, CD$_3$OD) δ: 13.01 (CH$_3$), 22.85 (CH$_3$CH$_2$), 29.78 ((CH$_2$)$_{12}$), 39.04 (CH$_2$NH), 40.33 (CH$_2$NHCH), 41.28 (CH$_2$NH$_2$), 52.87 (CHNH, CHNH$_2$), 63.90 (OCH$_2$CH), 71.45 (OCH$_2$CHO), 157.0 (NHCOO), 169.0 (NHCOCH). IRv/cm$^{-1}$:3430 ($v_{NH}$), 2920 ($v_{CH}$), 1670 ($v_{C=O}$), 1255 ($v_{CN}$).

Example 4

A synthesis method of the cationic peptide lipid compound R$_{18}$AOKK is as follows.

(1) 20 mmol L-Ala was weighted and dissolved in 100 ml of acetonitrile; 40 mmol Boc$_2$O was dissolved in acetonitrile and added dropwise to the acetonitrile solution of Ala; the mixture was stirred and reacted at room temperature for 2 hours, and then the solvent was removed by rotary evaporation at 70° C., followed by recrystallization with an ethyl acetate/petroleum ether mixed solvent, to obtain a peptide head intermediate L-Ala (Boc)-OH.

(2) 15 mmol 3-amino-1,2-propanediol was dissolved in 80 ml acetone, 10 mmol sodium bicarbonate was added, and then 40 mmol Fmoc-OSul was dissolved in 80 ml of acetone, slowly added dropwise and stirred overnight. Acetone was distilled off by rotary evaporation. 10 mmol of the above product was dissolved in a dichloromethane solvent; 14 mmol CDI was dissolved in toluene, and the two were slowly added dropwise under protection by nitrogen to react at 40° C. for 24 hours. 10 mmol octadecylamine was dissolved in 10 ml toluene solution, and the mixture was slowly added dropwise to the aforesaid reaction solution, and reaction was further carried out at 40° C. for 48 hours. 2.0 mmol sodium hydroxide was added to the reaction solution to react for 2 h. After completion of the reaction, the solvent was removed by rotary evaporation at 70° C., followed by recrystallization with acetonitrile/water (v/v=5:1), to obtain pale yellow solid, which was dried under vacuum. The resultant was recrystallized with DMF once again, to obtain a double long carbon chain intermediate $R_{18}$.

(3) The prepared peptide head intermediate L-Ala (Boc)-OH and an activating agent HATU were dissolved at a molar ratio of 1:2 in a toluene solution, and the activation was carried out at room temperature for 2 hours, and then a toluene solution of the long carbon chain intermediate $R_{18}$ was added so that the peptide head intermediate reacted with the long carbon chain intermediate according to a molar ratio of 1:2, followed by amidation reaction at 40° C. for 48 hours; after the reaction was completed, the solvent was removed by rotary evaporation at 70° C. The resultant was dissolved with 10 ml trifluoroacetic acid solvent, and placed at 4° C. for 2 hours to release the protective group Boc; then the product was dissolved by 20 ml 10% $NaHCO_3$ solvent and reacted for 0.5 hour, to remove Fmoc group.

(4) The product was recrystallized with acetonitrile twice and then recrystallized twice with a mixture solvent of ethanol and water (volume ratio 5:1). After that, the product was dissolved in chloroform, and the crude product was purified by a silica gel column and then was eluted with a methanol/chloroform (volume ratio 3:1) mixed reagent. The solvent was removed by rotary evaporation at 70° C., and the resultant was lyophilized, to obtain a propyl cationic peptide lipid compound containing one alanine head.

(5) 10 mmol L-Orn was weighted and dissolved in 15 ml of acetonitrile; 80 mmol $Boc_2O$ was dissolved in acetonitrile, and the mixture was added dropwise to an acetonitrile solution of ornithine, and a complex was generated after reaction; 20 ml 20% sodium bicarbonate aqueous solution was added, and 2 g of anhydrous sodium carbonate and an appropriate amount of 8-hydroxyquinoline were added in batches; the mixture was stirred and reacted at room temperature for 4 hours to remove copper ions in the complex; then 10 mmol Fmoc-OSu was added to the aforesaid solution, followed by stirring at room temperature for 2 hours; the resultant was recrystallized with an ethyl acetate/petroleum ether system, to obtain a peptide head intermediate Fmoc-L-Orn (Boc)-OH.

(6) The cationic peptide lipid compound containing one alanine head prepared in step (4) was taken as a raw material to react with the amino protected ornithine heat intermediate Fmoc-L-Orn (Boc)-OH prepared in step (5) at a molar ratio of 1:4, followed by amino acid activation and amidation; wherein the specific reaction conditions and purification method are the same with steps (3) and (4). That is, a propyl cationic peptide lipid containing an Ala-Orn dipeptide cationic head, and an 18C double long carbon chain was obtained.

(7) 5 mmol L-Lys was weighted and dissolved in 30 ml of acetonitrile; 5 mmol $Boc_2O$ was dissolved in acetonitrile, and then the mixture was added dropwise to an acetonitrile solution of lysine; 1 mmol copper sulfate pentahydrate was added, and a $(LysBoc)_2Cu$ complex was generated after the reaction; 10 ml 20% sodium bicarbonate aqueous solution was added, and 2 g of anhydrous sodium carbonate and an appropriate amount of 8-hydroxyquinoline were added in batches; the mixture was stirred and reacted at room temperature for 4 hours to remove copper ions in the complex; then 5 mmol Fmoc-OSu was added to the aforesaid solution, followed by stirring at room temperature for 2 hours; the resultant was recrystallized with an ethyl acetate/petroleum ether system, to obtain a peptide head intermediate Fmoc-L-Lys (Boc)-OH.

Figure 7:
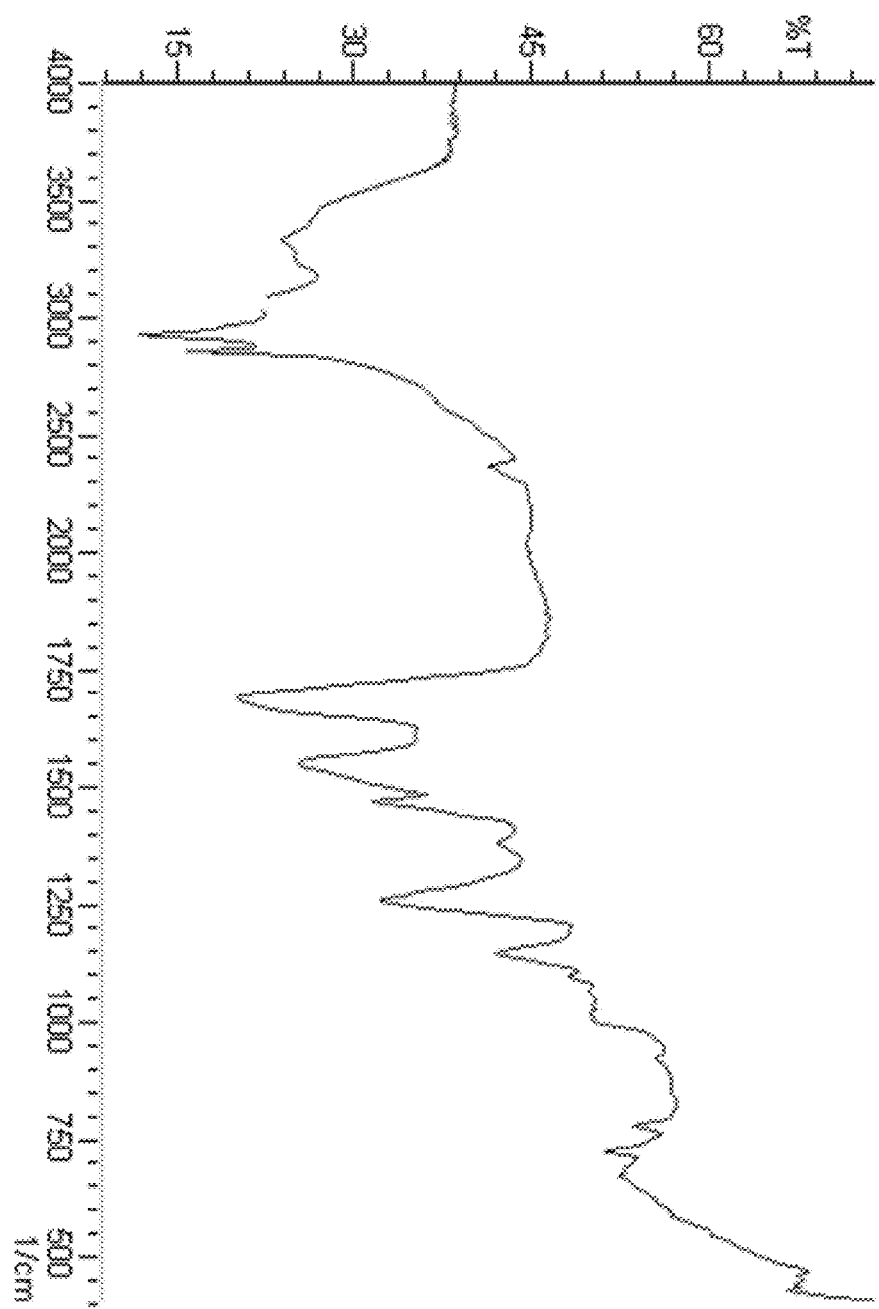
FIG. 7 is an infrared spectra of a propyl peptide lipid compound $R_{18}AOKK$.
Figure 8:
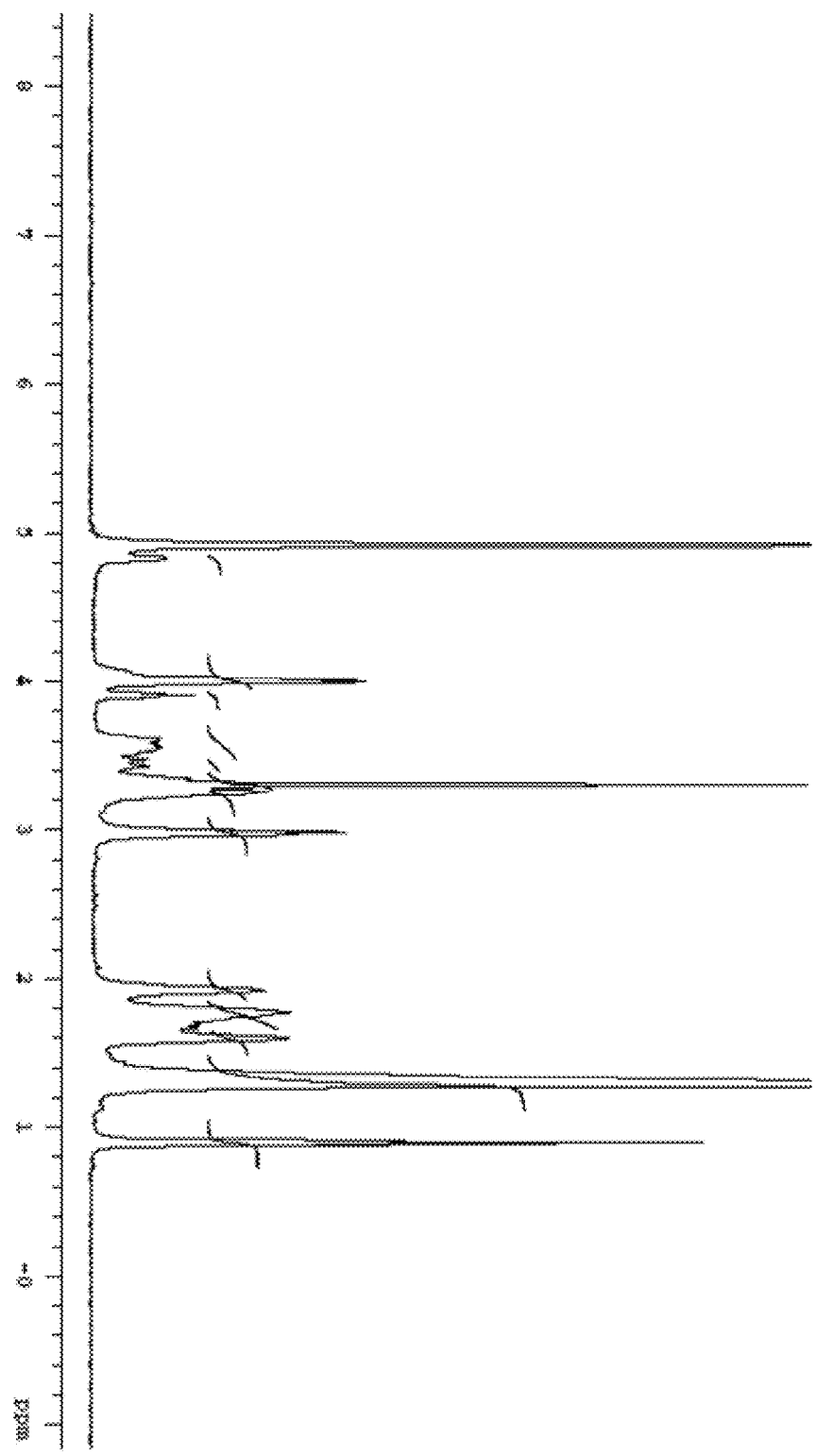
FIG. 8 is a nuclear magnetic resonance hydrogen spectrum of a propyl peptide lipid compound $R_{18}AOKK$.

(8) The cationic peptide lipid compound containing an Ala-Orn dipeptide head prepared in step (6) was taken as a raw material to react with the amino protected lysine peptide head intermediate Fmoc-L-Lys (Boc)-OH prepared in step (7) at a molar ratio of 1:8, followed by amino acid activation and amidation; wherein the specific reaction conditions and purification method are the same with steps (3) and (4). That is, a propyl cationic peptide lipid $R_{18}AOKK$ containing four amino acid heads, and an 18C double long carbon chain was obtained, of which the structural characterization is shown by FIG. 7 and FIG. 8.

Its structural characteristics are as follows: $^1H$ NMR (400 MHz, $CD_3OD$) δ: 0.88 (6H, $CH_3$), 1.28 (60H, $(CH_2)_{15}$), 2.94 (4H, $CH_2NH_2$), 3.16 (8H, $CH_2NH$), 3.34 (2H, $OCHCH_2$), 3.92 (2H, $CHNH_2$), 4.15 ($2H_2OCH_2CH$), 4.33 (1H, CHNH), 4.89 ($1H_2OCHCH_2$). $^{13}C$ NMR (400 MHz, $CD_3OD$) δ: 13.12 ($CH_3$), 22.65 ($CH_3CH_2$), 28.85 ($(CH_2)_{16}$), 39.13 ($CH_2NH$), 40.34 ($CH_2NHCH$), 40.99 ($CH_2NH_2$), 52.72 (CHNH, $CHNH_2$), 63.78 ($OCH_2CH$), 71.25 ($OCH_2CHO$), 157.10 (NHCOO), 169.0 (NHCOCH). $IRv/cm^{-1}$: 3435 ($v_{NH}$), 2925 ($v_{CH}$), 1675 ($v_{C=O}$), 1255 ($v_{CN}$).

From Example 1 to Example 4, it is easy for a person skilled in the art to see that all of the respective propyl cationic peptide lipids according to the invention and an alkyl alcohols feedstock can generate a propyl long carbon chain intermediate via acylating 3-amino-1,2-propanediol with an acylating agent diethylenetriamine, and that the intermediate undergoes the condensation reaction with a carboxyl group of an amino acid through esterification and amidation, to generate a propyl cationic peptide lipid containing 1 to 8 amino acids, followed by a series of similar separation and purification methods to remove impurities to obtain a pure product.

Example 5 Preparation of a Cationic Peptide Liposome Using $R_{12}O$ 1 mg a cationic peptide lipid $R_{12}O$ was weighted and was dissolved together with cholesterol at a molar ratio of 8:1 in 1 ml trichloromethane solvent; after they were fully dissolved, the resultant solution was blown into a uniform thin film under nitrogen, and dried in vacuum for 12 hours so that the solvent totally volatilized (at a vacuum degree of −0.09 MPa, room temperature); 1000 μl of ultrapure water was added to perform hydration at about 80° C. for 2 hours; then, ultrasonic vibration was performed at the ultrasonic frequency of 100 Hz to be clear and transparent, to obtain a cationic peptide liposome in the concentration of 1 mg/ml.

Example 6 Preparation of a Cationic Peptide Liposome Using $R_{14}AO$ 0.5 mg of a cationic peptide lipid $R_{14}AO$ was weighted and dissolved in 1 ml trichloromethane, and then a sucrose ester (a molar ratio of $R_{14}AO$ to sucrose ester is 1:1) was added; after they were fully dissolved, the resultant solution was blown into uniform thin film under nitrogen, and dried in vacuum for 4 hours so that the solvent totally volatilized (at a vacuum degree of −0.09 MPa, room temperature); the resultant product was immersed with 1 ml of ultrapure water for 6 hours to release the film, which was subjected to ultrasonic vibration at 20° C. (at the ultrasonic frequency of 100 Hz) to be clear and transparent, to obtain a cationic peptide liposome in the concentration of 0.5 mg/ml.

Example 7 Preparation of a Cationic Peptide Liposome Using $R_{16}OKK$ 1.5 mg a cationic peptide lipid $R_{16}OKK$ was weighted and was dissolved together with a co-lipid DOPE (a molar ratio of $R_{16}OKK$ to DOPE is 2:1) in 1 ml trichloromethane; after they were fully dissolved, the resultant solution was blown into uniform thin film under nitrogen, and dried in vacuum for 8 hours so that the solvent totally volatilized (at a vacuum degree of −0.09 MPa, room temperature); 1 ml phosphate buffer was added to perform hydration for 4 hours; then, ultrasonic vibration was performed at 55° C. at the ultrasonic frequency of 100 Hz to be clear and transparent, to obtain a cationic peptide liposome $R_{16}OKK$ in the concentration of 1.5 mg/ml.

Example 8 Preparation of a Cationic Peptide Liposome Using $R_{18}AOKK$

A cationic peptide lipid $R_{18}AOKK$ and DOPC (the cationic peptide liposome was 3 mg) at a molar ratio of 3:1 were accurately weighted and dissolved in 1 ml a mixture solvent of methanol and trichloromethane, wherein methanol:trichloromethane=1:2 (volume ratio); after they were fully dissolved, the resultant solution was blown into uniform thin film under nitrogen, and dried in vacuum for 5 h so that the solvent totally volatilized (at a vacuum degree of −0.09 MPa, room temperature); then, 200 μl absolute ethanol at approximately 55° C. was added to release the film; 800 μl a buffer was added, and ultrasonic vibration was repeatedly performed at about 35° C. (at the ultrasonic frequency of 100 Hz) to be clear and transparent, to obtain a cationic peptide liposome in the concentration of 3 mg/ml.

Example 9 Measurement of Particle Size and Zeta Potential of Liposomes

Figure 9:
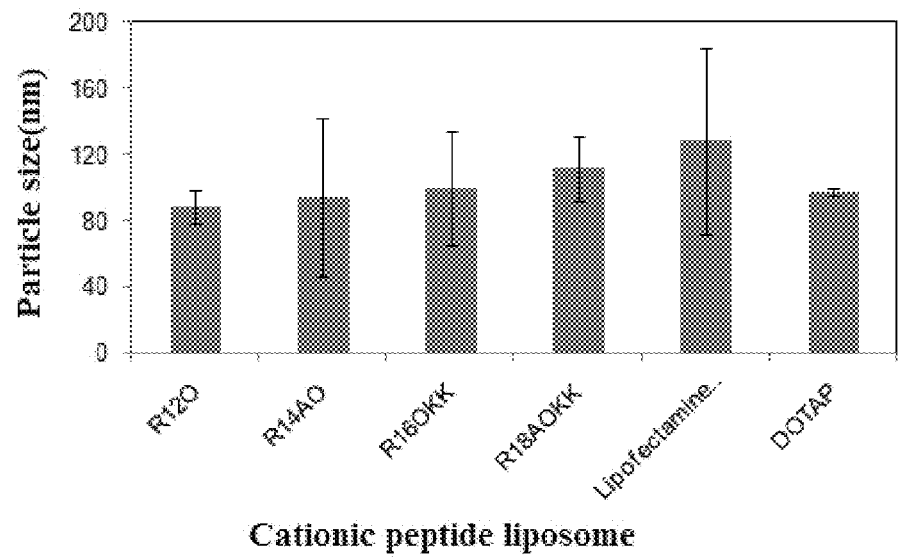
FIG. 9 is a particle-size diagram of propyl peptide liposomes.
Figure 10:
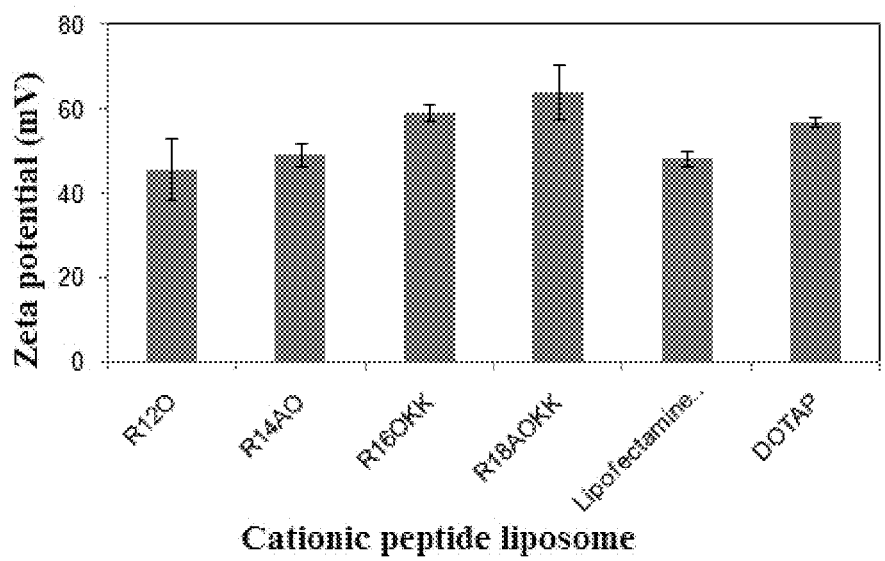
FIG. 10 is a Zeta potential diagram of propyl peptide liposomes.

Particle Size and Zeta potential of the prepared cationic peptide liposomes were measured using a laser scattering particle size analyzer (HORIBA nanoparticle size analyzer SZ-100) under conditions of 25° C. and a light scattering angle of 90°. 20 μl of the cationic peptide liposomes prepared in Example 5 to Example 8 were taken by a pipette and diluted in 1 ml ultrapure water; they respectively underwent measurement of particle size and Zeta potential, and the results are shown in FIG. 9 and FIG. 10. FIG. 9 shows average particle size of four kinds of propyl peptide liposomes, and FIG. 10 shows Zeta potential of four kinds of propyl peptide liposomes.

As shown by the results, the liposomes formed from the four kinds of propyl cationic peptide lipids all had a particle size of about 100 nm, within the range of effective particle size for transfection(<1 μm), and the Zeta potential was positive, and its absolute value was larger than 30 mV, which proves that the liposomes had relatively good electrostatic stability.

Example 10 Preparation of a $R_{12}O$ Liposome/DNA Complex

A propyl cationic peptide liposome was prepared in the method as mentioned in Example 5. 0.5 μg of the 1 mg/ml liposome $R_{12}O$ was taken and diluted with a serum-free DMEM culture medium to 25 μl; 0.5 μg of 0.5 mg/ml plasmid DNA was taken and diluted with a serum-free DMEM culture medium to 25 μl; the two dilutions (a mass ratio of the liposome to DNA is 1:1) were mixed and slightly vortexed, incubated at room temperature for 10 min, to obtain a $R_{12}O$ liposome/DNA complex.

Example 11 Preparation of a $R_{14}AO$ Liposome/DNA Complex

A propyl cationic peptide liposome was prepared in the method as mentioned in Example 6. 1 μg of the 0.5 mg/ml liposome $R_{14}AO$ was taken and diluted with a serum-free DMEM culture medium to 25 μl; 0.5 μg of 0.5 mg/ml plasmid DNA was taken and diluted with a serum-free DMEM culture medium to 25 μl; the two dilutions (a mass ratio of the liposome to DNA is 2:1) were mixed and slightly vortexed, incubated at room temperature for 20 min, to obtain a $R_{14}AO$ liposome/DNA complex.

Example 12 Preparation of a $R_{16}OKK$ Liposome/DNA Complex

A propyl cationic peptide liposome was prepared in the method as mentioned in Example 7. 3.0 μg of the 1.5 mg/ml liposome $R_{16}OKK$ was taken and diluted with a serum-free DMEM culture medium to 25 μl; 0.5 μg of 0.5 mg/ml plasmid DNA was taken and diluted with a serum-free DMEM culture medium to 25 μl; the two dilutions (a mass ratio of the liposome to DNA is 6:1) were mixed and slightly vortexed, incubated at room temperature for 30 min, to obtain a $R_{16}OKK$ liposome/DNA complex.

Example 13 Preparation of a $R_{18}AOKK$ Liposome/DNA Complex

A propyl cationic peptide liposome was prepared in the method as mentioned in Example 8. 4.0 μg of the 3.0 mg/ml liposome $R_{18}AOKK$ was taken and diluted with a serum-free DMEM culture medium to 25 μl; 0.5 μg of 0.5 μg/μl plasmid DNA was taken and diluted with a serum-free DMEM culture medium to 25 μl; the two dilutions (a mass ratio of the liposome to DNA is 8:1) were mixed and slightly vortexed, incubated at room temperature for 40 min, to obtain a $R_{18}AOKK$ liposome/DNA complex.

Example 14 Preparation of a Propyl Cationic Peptide Liposome/siRNA Complex

Propyl cationic peptide liposomes were prepared in the methods as mentioned in Example 5 to Example 8. 0.9 μg of the 1 mg/ml $R_{14}AO$ was taken and diluted with a serum-free DMEM culture medium to 25 μl; 0.3 μg of the 0.3 μg/μl siRNA was taken and diluted with a serum-free DMEM culture medium to 25 μl; the two dilutions (a mass ratio of the liposome to siRNA is 3:1) were mixed and slightly vortexed, incubated at room temperature for 20 min, to obtain a $R_{14}AO$ liposome/siRNA complex.

Figure 11:
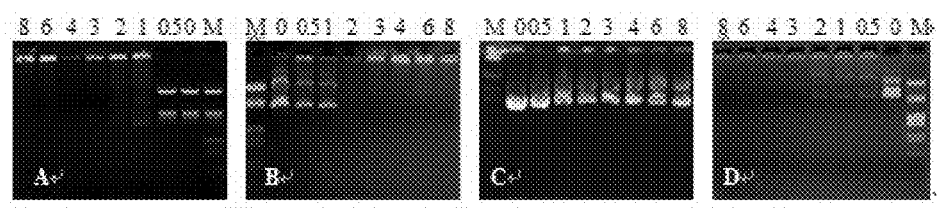
FIG. 11 is a diagram showing detection of the binding capacity of propyl peptide liposomes to plasmid DNA.

Example 15 Electrophoretic Delay Experiment of the Combination of a Liposome and a Plasmid DNA Agarose gel electrophoresis delay experiment was employed to detect corresponding charge ratios upon different mass ratios of the propyl cationic peptide liposomes to the plasmid DNA and further obtain an effective ratio for compression. The peptide liposomes and the plasmid DNA were diluted in 25 µl of a serum-free DMEM culture medium respectively according to a mass ratio being 0:1, 0.5:1, 1:1, 2:1. 3:1, 4:1, 6:1, 8:1; the dilutions were mixed and slightly vortexed, incubated at room temperature for 20 min; 2 µl of 6×DNA loading buffer was added in order to 20 µl of the above-mentioned complexes of peptide liposomes and plasmid DNA; the mixtures were uniformly mixed and loaded in order in loading holes of 1.2% agarose gel; the voltage was set to be 90 V to perform electrophoresis for 40 minutes. A nucleic acid dye solution NA-Red was added when the gel was prepared, so the DNA delay was directly observed in a gel imaging system Gene Genius Bio-imaging System (SYNGENE company). Electrophoresis results are shown in FIG. 11. Wherein, lanes 1 to 8 correspond to liposome/DNA complexes in which the mass ratios of the cationic peptide liposomes to DNA are 0:1, 0.5:1, 1:1, 2:1, 3:1, 4:1, 6:1, 8:1, respectively. A is an electrophoretogram of the combination of a propyl peptide liposome $R_{16}OKK$ and DNA, B is an electrophoretogram of the combination of a propyl peptide liposome $R_{18}AOKK$ and DNA, C is an electrophoretogram of the combination of a propyl peptide liposome $R_{12}O$ and DNA, and D is an electrophoretogram of the combination of a propyl peptide liposome $R_{14}AO$ and DNA.

As shown by results in FIG. 11, peptide liposomes prepared from $R_{16}OKK$, $R_{18}AOKK$ and $R_{14}AO$ all can effectively compress pDNA. Along with gradual increase in the concentration of the peptide liposomes, free DNA bands are gradually weakened, and when N/P is larger than 2:1, DNA can be completely compressed by the liposome. The liposome prepared from $R_{12}O$ has relatively poor capability of compressing DNA.

Example 16 In Vitro Biological Evaluation Experiments (1) Experiment of Carrying pGFP-N2 Plasmid to Transfect Cells Hep-2 cells were seeded in a 24-well cell culture plate; the cell concentration per well was about $1.0 \times 10^5$; after incubation for 24 h, the cell density became 80 to 90% on the transfection date. The liposome and the pGFP-N2 plasmid were combined respectively according to a ratio of 1:1, 2:1, 3:1, 4:1, 6:1 and 8:1, and the total volume after the combination was 100 µl. The resultant complexes were added to a cell culture plate and cultured for 4 to 5 hours; then the culture medium was replaced with a culture medium containing 10% serum and antibiotics, followed by culturing for 48 hours. A product GFP expressed by a green fluorescent protein gene could lase green fluorescence with a peak of 508 nm. An inverted fluorescence microscope was used to analyze the gene expression. Positive cells emitted bright green fluorescence, while negative cells none. The more GFP positive cells are, the stronger signal becomes, indicating higher transfection efficiency. The observation magnification is 20×10.

Figure 12:
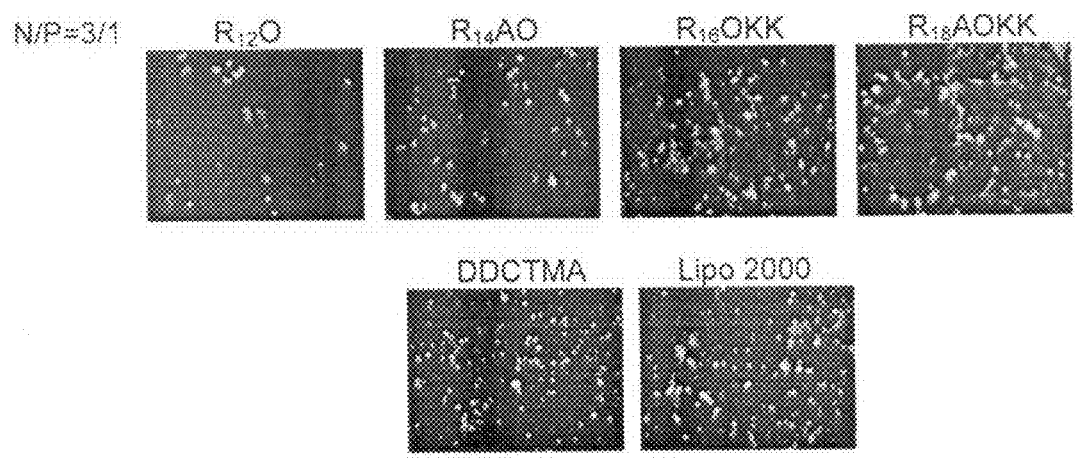
FIG. 12 is a diagram showing the green fluorescent protein expression in Hep-2 cells transfected by propyl peptide liposomes carrying plasmid pGFP-N2.

The results are shown in FIG. 12. When the mass ratio of the liposome and DNA was 3:1, the liposome could transfect Hep-2 cells at high efficiency, and the intensity of the green fluorescence is obviously higher than that of the urethane-type cationic liposome DDCTMA, and the intensity of the green fluorescence protein is significantly increased as compared with a commercial reagent Lipofectamine 2000.

(2) Experiment of Carrying pGL-3 Plasmid to Transfect Cells

The method of culturing cells is the same as the above-mentioned step (1). The liposome and the pGL-3 plasmid were combined respectively according to a ratio of 1/1, 2/1, 3/1, 4/1, 6/1 and 8/1, and the total volume after the combination was 100 µl. The resultant complexes were added to a cell culture plate, which was gently shaken to mix the complexes uniformly. Then, culturing was performed under 5% $CO_2$ (incubator) at 37° C. for 4 to 5 hours; then the culture medium was replaced with a culture medium containing 10% serum and antibiotics, followed by culturing for 48 hours. After the transfection, the cells were washed with DPBS once; 600 µl lysate was added to each well; after 20 min, the cells were transferred to a 96-well whiteboard, and 80 µl Promega E151A detection fluid was added to each well. The relative enzyme activity was detected by Synergy 2 multifunctional microplate reader (BioTek). The total protein content was measured using Pierce BAA Protein Assay kit of Thermo Electron as a standard control. After the measurement of protein, the transfection efficiency can be expressed as RLU/mg protein.

Figure 13:
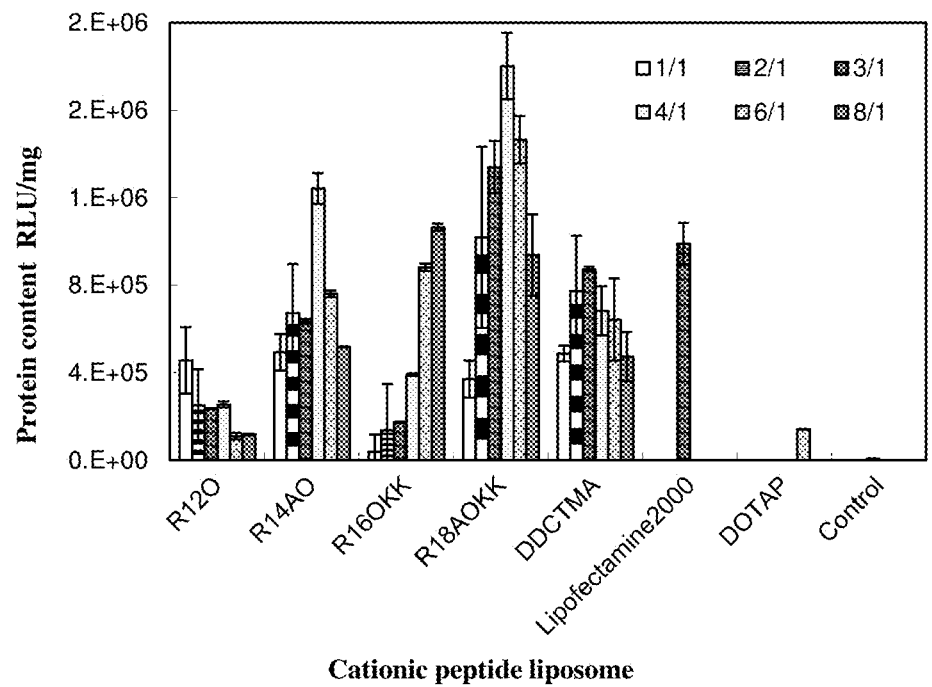
FIG. 13 is a diagram showing the luciferase expression in Hep-2 cells transfected by propyl peptide liposomes carrying plasmid pGL-3, detected by a microplate reader.

Results of the experiments are shown in FIG. 13. The four liposomes all can carry pGL3 plasmid to transfect Hep-2 cells, and the transfection efficiency was higher than that of the urethane-type cationic liposome DDCTMA. Wherein, the liposome $R_{16}OKK$ had the highest transfection efficiency when N/P was 4:1, and it was 2.5 times as high as the transfection efficiency of the urethane-type cationic liposome DDCTMA, it was twice as high as the transfection efficiency of the commercial reagent Lipofectamine 2000, and it was 10 times as high as the transfection efficiency of DOTAP.

(3) RNA Interference Experiments

Cell plating was not counted, and substantially confluent A549 cells were taken and added to a 12-well plate by 2 ml per well, and cultured for 24 h to a cell density of about 50 to 60%. 200 µl of a liposome/siRNA complex was added to each well to perform transfection for 18 h; then, the resultant product was changed to be cultured in a growth culture medium for 30 h. Then, the cells were washed with DPBS once; 600 µl lysate was added to each well; after 20 mins, 20 µl cells per well were transferred to a 96-well whiteboard, and 80 µl promega E151A detection fluid was added to each well. The relative enzyme activity was detected by a multifunctional microplate reader (BioTek). 5 µl lysate was added to a 96-well transparent plate, and a total protein content was measured using Pierce BAA Protein Assay kit of Thermo Electron as a standard control.

Figure 14:
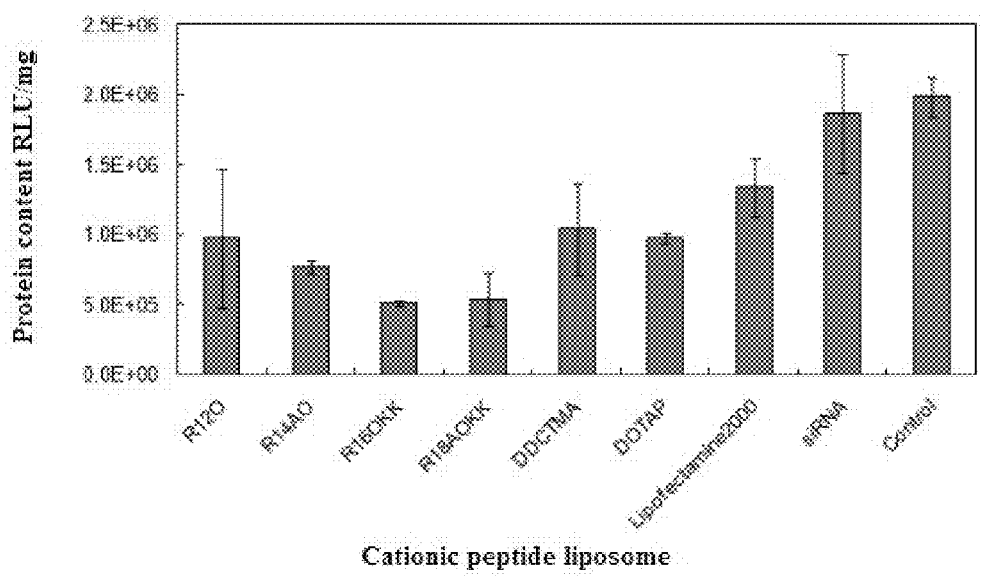
FIG. 14 is a diagram showing Luciferase gene silencing in A549 cells transfected by propyl peptide liposomes carrying siRNA.

FIG. 14 shows the capability of silencing Luciferase gene when A549 cells were transfected by four kinds of propyl peptide liposomes carrying siRNA. siRNA and Control are controls. As shown by the results, after A549 cells were transfected by the four kinds of propyl peptide liposomes, the expression level of Luciferase gene were inhibited to different degrees, and the silencing efficiency increased by about 40 to 50% as compared with the commercial reagent Lipofectamine 2000. Wherein, liposome $R_{16}OKK$/siRNA and $R_{18}AOKK$/siRNA resulted in the luciferase gene silencing efficiency of 60 to 75% as compared with the blank control, and resulted in the significantly improved silencing efficiency, compared with the urethane-type cationic liposome/gene complex DDCTMA and the commercial reagent DOTAP.

(4) Study of Cytotoxicity (MTT Colorimetry)

MTT method was used to perform cytotoxicity test on cationic liposomes having the relatively high transfection efficiency, and the commercial cell-transfecting reagents Lipofectamine 2000 and DOTAP were taken as controls. Hep-2 cells were seeded in a 96-well cell culture plate, and 100 μl cell culture medium (containing double antibody and serum) was added to each well, the concentration being about $1.0 \times 10^6$ cells per well; culturing was performed for 24 hours so that the cell density became 80 to 90% on the transfecting date. The growth culture medium was removed, and the resultant was washed with 100 μl culture medium, which was then replaced with equivalent (100 μl) culture medium. The liposomes and the plasmid DNA were combined according to a ratio of 1:1, 2:1, 3:1, 4:1, 6:1, 8:1, respectively and added to a cell culture plate. After cell culture for 24 hours, 20 μl MTT (Sigma, 5 mg/ml) was added to each well to culture and incubate for 4 to 4.5 h. Then the culture medium was discarded, and 150 μl DMSO was added to make cells lysis, and its absorbance was measured by microplate reader at a wavelength of 570 nm. Taking the absorbance of the blank control (non-transfected cells) as 100%, percentage of survival transfected cells was calculated according to a calculation formula: cell survival rate $(\%) = [A]_{sample}/[A]_{control} \times 100\%$.

Figure 15:
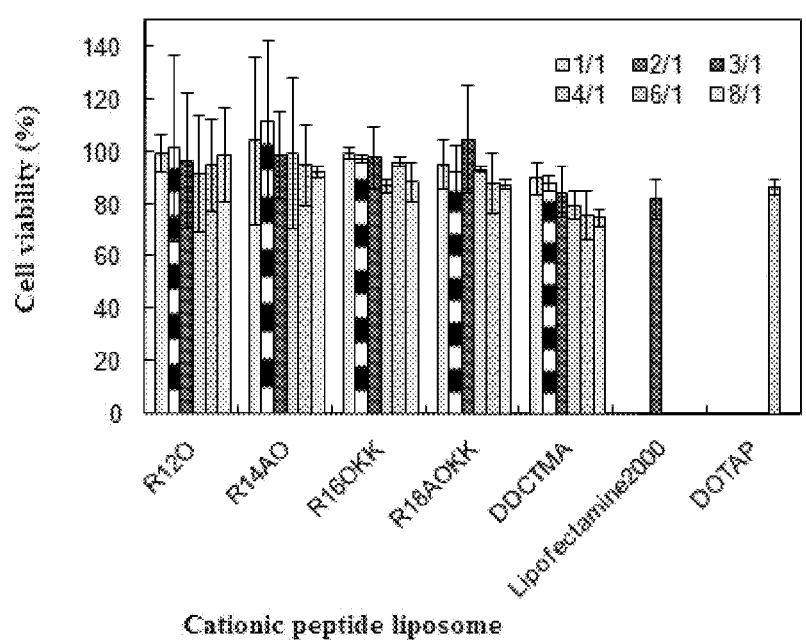
FIG. 15 is a diagram showing cytotoxicity to Hep-2 during cells transfection by cationic peptide liposomes, detected by MTT colorimetry.

The experiment results are shown in FIG. 15, in which the horizontal ordinate represents the prepared propyl cationic peptide liposomes, and the mass ratio of the liposomes to DNA is 1:1 to 8:1. The four liposomes all had little toxicity to Hep-2 cells, and the cell survival rates were 90 or more. The cell survival rates were significantly improved, compared to the urethane-type cationic lipid gene complex (DDCTMA), the commercial reagents Lipofectamine 2000 and DOTAP.

The invention claimed is:
1. A propyl cationic peptide lipid having a structure of general formula I:

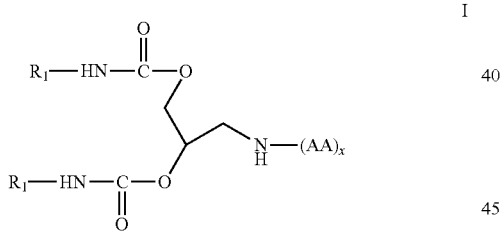

wherein,
$R_1$ is selected from $C_{1-20}$ alkyl, x is an integer from 1 to 6, and $(AA)_x$ represents an amino acid selected from the group consisting of lysine (Lys), ornithine (Orn), arginine (Arg), histidine (His), aspartic acid (Asp), and alanine (Ala), or a peptide comprising Orn and at least one amino acid selected from the group consisting of Lys, Orn, Arg, His, Asp, Ala, and glycine (Gly).

2. The propyl cationic peptide lipid according to claim 1, wherein $R_1$ is selected from $C_{12}$, $C_{14}$, $C_{16}$, or $C_{18}$ alkyl, x is selected from 2 to 4.

3. A method for synthesizing a propyl cationic peptide lipid, comprising the following steps:
1) preparing a peptide head intermediate by protecting amino group of amino acid with a protective reagent by means of orthogonal protection method: the amino acid being selected from Lys, Orn, Arg, His, Asp, Ala or Gly, the amino group protective reagent being di-tert-butyl dicarbonate (Boc2O), Fluorenylmethoxycarbonyl succinimide (Fmoc-OSu) or benzyl chloroformate (CbzCl), at a molar ratio of the protective reagent and the amino acid being 1:1 to 8:1, the reaction solvent being acetonitrile, toluene, acetone, tetrahydrofuran or water, the reaction time being 1 to 20 hours, and the reaction temperature being 0 to 100° C., after the reaction, the solvent being removed by rotary evaporation, followed by purification by means of recrystallization with a recrystallization solvent being an ethyl acetate/petroleum ether mixed solvent (v/v=3:1);
2) protecting the amino group of 3-amino-1,2-propanediol with Fmoc-OSu protective reagent, after acylation with an acylating agent, reacting the resultant with alkyl amine, to prepare a disubstituted propyl long carbon chain intermediate: the acylating agent being carbonyl diimidazole, at a molar ratio of the acylating agent and 3-amino-1,2-propanediol being 1:1 to 3:1, after acylation, the molar ratio of 3-amino-1,2-propanediol to the alkyl amine being from 1:1 to 8:1, the reaction solvent being 30 ml to 300 ml of toluene, dichloromethane, DMF or chloroform, the reaction time being 12 to 48 hours, the reaction temperature being 25-100° C., after the reaction, the solvent being removed by rotary evaporation at 70° C., recrystallization being carried out with DMF, ethanol, ethyl acetate, water or ethanol/water mixed solvent;
3) linking the peptide head intermediate prepared in step (1) with the double long carbon chain intermediate prepared in step (2) via acylation:
  a. activating the peptide head intermediate firstly with an activating agent which is 2-(7-azobenzotriazole)-N,N,N',N'-tetramethyluronium hexafluorophosphate (HATU), N,N'-dicyclohexyl carbonimide (DCC) or 1-hydroxybenzotriazole (HOBt), at a molar ratio of the peptide head intermediate to the activating agent being 1:1 to 1:8, the reaction temperature being 0 to 60° C., the reaction time being 0.5 to 24 hours;
  b. adding a solution of the double long carbon chain intermediate in dichloromethane, DMF or chloroform to the reaction solution in step a, after acylation, an amide bond being generated between the amino group of the intermediate and the carboxyl group of the peptide head intermediate, the peptide head intermediate reacting with the double long carbon chain intermediate at a molar ratio of 1:1 to 8:1, the reaction solvent being toluene, DMF, chloroform, acetone or methylene chloride, the reaction time being 12 to 96 hours, the reaction temperature being 20 to 100° C.;
4) removing the protective group with an amino de-protection agent which is 10% $NaHCO_3$ (w/v) or trifluoroacetic acid, at a molar ratio of the de-protection agent and a lipoid compound being 1:1 to 1:2, the de-protection time being 1 to 8 hours, the de-protection temperature being 0 to 4° C., the product being purified by recrystallization to obtain a crude product, the recrystallization solvent being ethyl acetate, acetonitrile, ethanol, water or anhydrous ether;
5) carrying out purification by column chromatography after the recrystallization, the crude product being dissolved in chloroform and purified with a silica gel column, followed by elution with a mixed solvent of methanol/chloroform (at a volume ratio of 3:1), the solvent being removed by rotary evaporation, followed by lyophilization, to obtain a cationic peptide lipid compound containing one amino acid head;
6) synthesizing other propyl cationic peptide lipid using the cationic peptide lipid compound containing one amino acid head as a raw material: subjecting the peptide head intermediate prepared in step (1) and the cationic peptide lipid containing one amino acid head prepared in step (5) to amino activation and acylation, to obtain a cationic peptide lipid compound of which the head is 1 to 6 amino acid(s), at a molar ratio of the two being 1:8 to 8:1, the specific reaction conditions and purification method being the same as steps (3), (4) and (5).

4. A cationic peptide liposome prepared from the propyl cationic peptide lipid according to claim 1, wherein the cationic peptide liposome is a homogeneous and stable liposome which is positively charged on the surface thereof and has a particle size of about 100 nm formed by dispersing the propyl cationic peptide lipid in an aqueous phase.

5. A method for preparing the propyl cationic peptide liposome, comprising the following steps:
   (1) dissolving a propyl cationic peptide lipid and an additive in chloroform or methanol according to a molar ratio of the two being 1:8 to 8:1, the additive being lecithin, sucrose esters, dioleoyl phosphatidylethanolamine (DOPE), dioleoyl phosphatidylcholine (DOPC) or cholesterol, wherein the propyl cationic peptide lipid has a structure of general formula I:

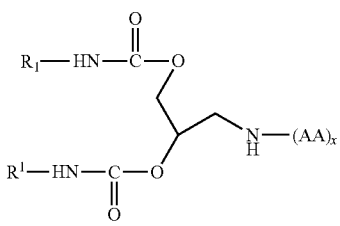

I wherein $R_1$ is selected from $C_{1-20}$ alkyl, x is an integer from 1 to 6, and $(AA)_x$ represents an amino acid selected from the group consisting of lysine (Lys), ornithine (Orn), arginine (Arg), histidine (His), aspartic acid (Asp), and alanine (Ala), or a peptide comprising Orn and at least one amino acid selected from the group consisting of Lys, Orn, Arg, His, Asp, Ala, and glycine (Gly);
   (2) blowing the solution under nitrogen to form a uniform thin film, and drying in vacuum for 4 to 24 hours;
   (3) performing hydration at 10 to 80° C. with ethanol, water or phosphate buffer for 1 to 10 hours, ultrasonic vibrating to transparent, to obtain the cationic peptide liposome with a concentration of 0.5 to 3 mg/ml.

6. A propyl cationic peptide liposome/gene complex prepared from the propyl cationic peptide liposome according to claim 4, wherein the propyl cationic peptide liposome according to claim 4 and plasmid DNA (pDNA) or small interfering RNA (siRNA), by electrostatic interaction form homogeneous and stable nanoparticles dispersed in an aqueous phase.

7. A method for preparing the propyl cationic peptide liposome/gene complex according to claim 6, comprising the following steps:
   (1) taking 0.5 to 8 μl the propyl cationic peptide liposome according to claim 4 and dispersing into 25 to 50 μl cell culture medium of DMEM or RPMI1640, mixing homogeneous to make a concentration being 0.02 μg/μl to 0.16 μg/μl;
   (2) diluting pDNA or siRNA in the cell culture medium DMEM or RPMI1640, mixing homogeneous 0.5 to 1.0 μl to make a plasmid concentration being 0.02 μg/μl;
   (3) mixing the two dilutions of (1) and (2) homogeneous according to a mass ratio between the liposome and gene of 1:1 to 8:1, placing at a room temperature for 10 to 40 min, to obtain the propyl cationic peptide liposome/gene complex.

8. A method for transfecting a cell, the method comprising applying the propyl cationic peptide liposome/gene complex according to claim 6 to the cell.

9. The propyl cationic peptide lipid according to claim 1, wherein $(AA)_x$ is -Ala-Orn.

10. The propyl cationic peptide lipid according to claim 1, wherein (AA)x is -Orn-Lys-Lys.

11. The propyl cationic peptide lipid according to claim 1, wherein $(AA)_x$ is -Ala-Orn-Lys-Lys.

* * * * *